United States Patent [19]

Chen et al.

[11] 4,385,126

[45] May 24, 1983

[54] DOUBLE TAGGED IMMUNOASSAY

[75] Inventors: Janet H. Chen, San Jose; Edward T. Maggio, Redwood City; Dietrich Rehbinder, Santa Clara, all of Calif.

[73] Assignee: International Diagnostic Technology, Inc., Santa Clara, Calif.

[21] Appl. No.: 217,011

[22] PCT Filed: Mar. 19, 1979

[86] PCT No.: PCT/US79/00184

§ 371 Date: Nov. 19, 1980

§ 102(e) Date: Nov. 19, 1980

[87] PCT Pub. No.: WO80/02076

PCT Pub. Date: Oct. 2, 1980

[51] Int. Cl.$^3$ ............... G01N 33/48; G01N 33/52; G01N 33/54

[52] U.S. Cl. ............... 436/518; 436/500; 436/508; 436/546; 436/800

[58] Field of Search ............... 424/8, 12; 23/230 B; 436/500, 508, 518, 546, 800

[56] References Cited

U.S. PATENT DOCUMENTS

| | | | |
|---|---|---|---|
| 3,959,650 | 5/1976 | Lukens | 250/303 |
| 3,993,741 | 11/1976 | Hermann | 424/1 |
| 3,996,345 | 12/1976 | Ullman | 424/12 |
| 3,998,943 | 12/1976 | Ullman | 424/8 |
| 4,011,308 | 3/1976 | Giaever | 424/1.5 |
| 4,174,384 | 11/1979 | Ullman | 424/8 |
| 4,220,450 | 9/1980 | Maggio | 424/12 X |

OTHER PUBLICATIONS

Chadwick, The Lancet, Feb. 22, 1958, pp. 412–414.

*Primary Examiner*—Anna P. Fagelson
*Attorney, Agent, or Firm*—Limbach, Limbach & Sutton

[57] ABSTRACT

Immunoassays are performed with two different ligands tagged with two different tagging constituents which are independent of each other and the two tagged ligands are immunologically bound together. The two different ligands may be detected independently through their independent tagging constituents for quality control, internal calibration (standardization), determination of viability and shelf life and the like.

6 Claims, No Drawings

DOUBLE TAGGED IMMUNOASSAY

TECHNICAL FIELD

This invention relates to techniques for diagnosing components of human blood and more particularly to a method of performing immunoassays.

BACKGROUND ART

A wide variety of techniques are known for performing immunoassays with a variety of tagging materials. Thus, immunologically active materials may be tagged with a radioactive element or a fluorescent constituent or a constituent which enters into an enzyme reaction. An immunoassay may be performed with any of these tagged materials with a variety of different immunoassay procedures. Thus a test material containing a suspected ligand may be analyzed and the ligand can be detected quantitatively by forming a complex of a tagged ligand, tagged as indicated above, with a receptor ligand and measuring the tagging constituent in the complex to deduce the quantity of the suspected ligand. The immunoassay may be performed in a number of ways, such as the well-known sandwich technique and the competitive and indirect techniques.

As used herein, the term "ligand" means any material which is capable of forming a ligand-receptor complex by means of protein interaction and the term is broad enough to include antigens and antibodies, binding proteins, haptens and hormone receptors.

The immunoassays of this invention employ at least three ligands. The three ligands are referred to as follows herein. First, there is the assay ligand which the assay has been designed to detect or measure. Second, there is the test ligand which is tagged as explained and is detected quantitatively in a complex to deduce a quantity of the assay ligand present. Thirdly, there is a receptor ligand which binds immunologically to the assay ligand and/or test ligand.

In the sandwich technique mentioned above, the assay ligand binds to immobilized receptor ligand to form a first complex. The tagged test ligand is then bound to the assay ligand in the complex to form the sandwich (the test ligand may be identical to the receptor ligand and often is), and the tagging constituent in the sandwiched ligands is detected quantitatively to deduce the quantity of assay ligand present. Detection can be performed by measuring radioactivity where the test constituent is radioactive or by measuring fluorescent light where there is a fluorescent constituent on the test ligand or spectrophotometrically where an optical density or wavelength change occurs through an enzyme reaction, or through fluorescent quenching. Detection may require separation of the sandwiched ligands from unbound ligands and this is generally done by separating the receptor ligand supported on a surface from a solution containing unbound test ligands.

The quantity of assay ligand is deduced from the quantity of test ligand detected, because the two quantities are generally directly proportional to each other in the sandwich technique. Parallel tests against known standards are employed for calibration.

The quantity of assay ligand may be deduced as as inverse proportion with the competitive technique mentioned above, where the assay ligand is contacting either simultaneously or sequentially with a known quantity of test ligand and a limiting quantity of receptor. Where the receptor and test ligands bind immunologically, the quantity of test ligand which is detected in a binary complex with the receptor is inversely proportional to the amount of assay ligand present.

In the indirect technique, a limiting amount of the test ligand will bind immunologically to either the assay ligand or the receptor ligand. The quantity of test ligand in binary complexes of test and receptor ligands is taken as an inverse measure of the quantity of assay ligand present in an equilibrium mixture of the three ligands.

The three techniques discussed above may be represented as follows where R designates the receptor ligand, A represents the assay ligand and T represents the test ligand.

| | | |
|---|---|---|
| 1. R + A → RA | | |
| 2. RA + T → RAT | | Sandwich |
| 1. R + A + T → RA + RT | simultaneous | } Competitive |
| 1. R + A → RA | | |
| 2. RA + T → RA + RT | sequential | |
| 1. A + T → AT | | |
| 2. AT + R → AT + RT | sequential | } Indirect |
| 1. A + T + R → AT + RT | simultaneous | |

In the preferred immunoassay methods of this invention, the test ligands are fluorescent materials, and the receptor ligand is bound to a surface on which a quantity of the test ligand is collected as a result of the interaction of the various ligands. Fluorescent measurement is made of the receptor and test ligands immunologically bound together on the surface. These preferred techniques employ fluorescent measurement of the surface, all as more fully described in the following U.S. Pat. Nos.: 3,992,631; 3,999,948; 4,020,151; 4,025,310; 4,056,724 and 4,067,959.

The various immunoassay techniques referred to above suffered from a variety of inaccuracies which result from inaccuracies in the amount of the receptor ligand which is present at any particular stage of operations. For instance, in the fluoro immunoassay techniques performed on the surface of an applicator, inaccuracies may occur in final test results where there are variations in the amount of the receptor ligand which is originally bound to the test surface. Similarly, inaccuracies can occur where some quantity of the receptor ligand is lost from the test surface during the course of shipment or the immunoassay procedure itself.

DISCLOSURE OF INVENTION

In accordance with this invention a dramatic improvement is obtained in quality control of immunoassay procedures and dramatic improvements are obtained in the convenience and accuracy of immunoassay procedures by binding to the receptor ligand a tagging constituent which remains independent of the tagging constituent of the test ligand and can be detected in the immunoassay independently of the tagging constituent on the test ligand.

Direct tagging of the receptor ligand in this way permits direct detection and measurement of the receptor ligand without interfering with the normal immunoassay procedure with the following advantages:

1. The tagging constituent on the receptor ligand can be used as a quality control to determine that a controlled amount of the ligand has been bound to a test surface during original manufacture of assay reagents.

2. Tests may be performed detecting the tagging constituent on the receptor ligand in a customer's laboratory to determine that reagents have not been damaged during transit and to calibrate an instrument for detection of the test ligand.

3. Finally, and possibly most importantly, the receptor ligand can be quantitatively detected during an immunoassay procedure independently of quantitative detection of the test ligand so that immunoassay procedures may be made self-calibrating.

Detection and measurement of the quantity of tagging constituent on the receptor ligand can be performed in known ways with known equipment as radioactive and fluorescent tags have been used heretofore. In designing the particular test, however, where it is intended to detect the receptor ligand prior to incubation of the receptor ligand with the other ligands, a tagging constituent on the receptor ligand should be used which will not interfere with the chemistry of the subsequent assay. Thus, where the receptor ligand is to be detected for quality control or for instrument calibration prior to incubation, it may be impractical to tag the receptor ligand with an enzyme tagging material.

A variety of pairs of tagging constituents can be used on the receptor and test ligands in a given assay where the two tagging constituents are independent of each other and can be detected independently of each other. Thus, one of the two ligands may be tagged with a fluorescent constituent while the other ligand is tagged with a radioisotope or enzyme tag. One of the ligands may be tagged with an enzyme tag while the other is tagged with either a radioisotope or a fluorescent tag, and one of the ligands may be tagged with a radioactive tag while the other ligand is tagged with a fluorescent or enzyme constituent. With suitable instrumentation other tagging constituents might be used which emit or absorb radiation of particular wavelengths.

Additionally, the receptor and test ligands may be tagged with similar types of tagging constituents which can be detected independently. For instance, one of the two ligands may be tagged with iodine 125 while the other is tagged with colbalt 57. Additionally, one of the ligands may be tagged with one fluorescent constituent, such as fluorescein isothiocyanate (FITC) while the other ligand may be tagged with a separate fluorescent constituent, such as tetraethylrhodamine isothiocyanate (RITC) or tetramethylrhodamine isothiocyanate (TRITC) where the two fluorescent constituents which are selected fluoresce at different wavelengths and thus may be detected separately.

In this invention, it is preferred to use two fluorescent constituents fluorescein and tetramethylrhodamine isothiocyanate because the test using those two fluorescent constituents may be performed in a very sensitive fluorometer presently available on the market simply by inserting in the fluorometer different filter assemblies for exciting and detecting the sample at different wavelengths.

The use of two-tagged ligands in accordance with this invention may be advantageous in a wide variety of immunoassays with a variety of different receptor and test ligands designed to detect a variety of different antigens, antibodies or haptens as assay ligands.

For example, assays may be performed in accordance with this invention with the following sets of receptor, test and assay ligands:

| Receptor-Tag | Test Ligand-Tag | Assay Ligand |
| --- | --- | --- |
| Anti-gentamicin-TRITC | Gentamicin-FITC | Gentamicin |
| Anti-tobramycin-TRITC | Tobramycin-FITC | Tobramycin |
| Anti-phenobarbital-TRITC | Phenobarbital-FITC | Phenobarbital |
| Anti-phenobarbital-TRITC | Phenobarbital-FA | Phenobarbital |
| Anti-theophylline-TRITC | Theophylline-FITC | Theophylline |
| Anti-diphenyl-hydantoin-TRITC | Diphenyl-hydantoin-FITC | Diphenylhydantoin |
| Anti-diphenyl-hydantoin-FITC | Diphenylhydantoin-Umbelliferone | Diphenylhydantoin |
| Anti-herpes-TRITC | Anti-herpes-FITC | Herpes Virus |
| Anti-CMV-TRITC | Anti-CMV-FITC | CMV |
| Anti-Acid phosphatase-TRITC | Anti-Acid phosphatase-FITC | Acid phosphatase |
| Anti-Acid phosphatase-TRITC | Acid phosphatase-FITC | Acid phosphatase |
| Rubella Antigen-TRITC | Anti-Human IgG-FITC | Human Anti-rubella |
| Rubella Antigen-TRITC | Anti-Human IgM-FITC | Human Anti-rubella |
| Digoxin-TRITC | Anti-digoxin-FITC | Digoxin |
| Anti-digoxin-TRITC | Digoxin-FITC | Digoxin |
| HEp-2 Cells-TRITC | Anti-human IgG-FITC | Human-Anti-nuclear Antibodies |
| Anti-digoxin-TRITC | Digoxin-protein-FITC | Digoxin |
| Anti-digoxin-FITC | Digoxin-protein-Umbelliferone | Digoxin |
| Anti-gentamicin-FITC | $^{125}$I Gentamicin | Gentamicin |
| Anti-gentamicin-$^{57}$Co | $^{125}$I Gentamicin | Gentamicin |
| Anti-gentamicin-FITC | Gentamicin-$\beta$-D-galactosidase | Gentamicin |
| Anti-gentamicin-Evans blue | Gentamicin-FITC | Gentamicin |
| Anti-gentamicin-FITC | Gentamicin-dansyl | Gentamicin |
| Anti-gentamicin-FITC | Gentamicin-coumarin 120 | Gentamicin |

Key:
FITC - fluorescein isothiocyanate
CMV - cytomegalovirus
TRITC - tetramethylrhodamine isothiocyanate
FA - fluorescein amine As indicated above, the invention permits certain immunoassays to be made self-calibrating. Thus, where a fluorescent measurement is made by illuminating a surface and quantitatively detecting fluorescent light emitted from the surface, there are a number of factors which may effect the optical gain at the interface between the surface and the fluorometer. Optical characteristics of the surface itself may effect the gain as, for instance, where the surface has a reflective undercoating. If the surface has a reflective undercoating, generally speaking fluorescent emission from the surface may be higher because (a) incident light passing through the surface passes back to augment fluorescent emission, and (b) fluorescent emission initially directed into the surface may be reflected out. Similarly, the gain at the optical interface may be effected by characteristics of the fluorometer, such as cleanliness of lenses, electronic gain or age of components and the like. The optical gain in the system may also vary depending upon a number of processing factors, such as the quantity of a reagent initially bound to the surface, shelf life of the product, vibratory damage during shipment and the like.

Because of the myriad of factors which may effect the gain between the surface fluorometer interface, it has been standard practice in many fluoro immunoassays to provide an extensive calibration procedure for calibrating the fluorometer with standardized surfaces periodically. With the preferred embodiment of this invention, the effect of gain variations at the surface—fluorometer interface may be compensated by cancelling out those variations as they appear in measurement of both tagging constituents. This is particularly effective where both tagging constituents are measured after incubation and also where the measurement is performed with the same instrument.

BEST MODE FOR CARRYING OUT THE INVENTION

Thus, in accordance with the preferred form of the invention, a fluorescent tag on the receptor ligand and a fluorescent tag on the test ligand are detected quantitatively, while they are bound to each other, and preferably by the same fluorometer, and the quantity of the assay ligand present in an unknown is determined as a function of the ratio of the quantitative measurements of the two tagging constituents. To the extent that any factor effecting the gain of the surface to fluorometer interface is the same in both measurements, the effect of that factor cancels out in the ratio eliminating the need for calibration to compensate for that factor.

In the following two examples, assays were performed using the competitive technique. Tagging constituents were used on both the receptor and test ligands, tetramethylrhodamine isothiocyanate tagged antibody for the receptor and fluorescein isothiocyanate tagged hapten for the test ligand.

EXAMPLE 1

Surface quality control and independent detection of receptor ligand during an immunoassay procedure were demonstrated in T4 assay. Tetramethylrhodamine isothiocyanate-anti T4 was prepared in the following way: to a solution of 250 $\mu$l of anti T4 IgG fraction from $(NH_4)_2SO_4$ precipitation, 24 mg/ml: and 100 $\mu$l of 0.1 M sodium phosphate, pH 9.72 was added 5 $\mu$l of TRITC (2.28 mg/ml in 0.1 M sodium phosphate pH 9.72 freshly prepared). The mixture was stirred at 4° C. overnight. The product was purified through a Sephadex G-50-150 column (14×1 cm), eluted with PBS pH 7.4. The eluate was collected in 10 drop fractions. The fractions containing the product were combined. The absorbance at 280 and 555 nm was measured. R/p was determined according to the following equation.

$$R/p = \frac{OD_{555} \times 12}{OD_{280} \times (1 - 0.88 \times OD_{555})}$$

$$R/p = 0.45$$

The resulting TRITC-anti T4 was diluted with unlabelled anti-T4 to R/p of 0.0084, 9.68 mg protein/ml (equivalent to unlabelled anti-T4 IgG fraction titer 2.5). 40 $\mu$l (287 $\mu$g) was spotted onto 10 samplers of the general type sold commercially by International Diagnostic Technology, Inc. under the trademark StiQ. The samplers used in these tests have a support surface with an area of approximately 0.283 square centimeters of periodate activated cellulose. The StiQ samplers were dried and reduced with $NaCNBH_3$. Fluorescent measurements were made of the StiQ samplers with the fluorometer sold by International Diagnostic Technology, Inc. under the trademark FIAX using a 540 nm filter in the excitation channel and a 570 nm filter in the emission channel. StiQ rhodamine signal was read both wet and dry after being soaked in 0.01 M borate 20 minutes. The StiQ's were incubated with 500 $\mu$l of 0.01 M borate pH 9 and FITC-T4 (7 ng T4 moiety by RIA) for 1 hour. The results are shown in the following table.

| StiQ No. | Rhodamine Signal soaked in borate 20 minutes | | Assay Signal gain 8 |
|---|---|---|---|
| | wet (gain 10) | dry (gain 2.5) | |
| 1 | 156 | 150 | 152 |
| 2 | 138 | 140 | 163 |
| 3 | 154 | 155 | 138 |
| 4 | 147 | 138 | 132 |
| 5 | 188 (gain 7.9) | 189 (gain 1.9) | 175 |
| 6 | 142 | 150 | 137 |
| 7 | 133 | 126 | 143 |
| 8 | 116 | 115 | 115 |
| 9 | 149 | 147 | 132 |
| 10 | 114 | 100 | 114 |
| S. Dev. | unedited[a] | 29.46 | 32.03 | 19.2 |
| | edited[b] | 8.38 | 10.6 | 11.4 |
| Mean | unedited[a] | 146.9 | 144.7 | 140.1 |
| | edited[b] | 145.6 | 144.5 | 142.4 |
| 11 | 22 | 12 | 136 |
| 12 | 21 | 12 | 156 |
| 13 | 73 | 83 | 62 |
| 14 | 75 | 86 | 67 |

[a] all StiQ's included
[b] underlined value excluded

| | CV's StiQ No. 1-10 | | |
|---|---|---|---|
| | Rhodamine CV's soaked in borate 20 minutes | | |
| | wet | dry | Assay CV's |
| 1-10 | 20% | 22% | 13.8% |
| 5.8.10 dropped | 5.8% | 7.4% | 8% |

The activity of anti T4 lightly labeled with TRITC is the same as unlabelled anti T4 (StiQ's 11 and 12 titer 2.5, 287 $\mu$g/StiQ). If the antibody—StiQ Schiff's base linkage is not reduced by $NaCNBH_3$ (StiQ's 13 and 14), the assay signal is decreased resulting from the detachment of antibody from the surface. This could be readily detected by the weakened rhodamine signal.

The nondestructive QC has pronounced effect on improving the CV's for assays using periodate oxidized paper. With QC, three outliers could be easily dropped, and the assay CV's were lowered from 13.8% to 8%.

EXAMPLE 2

In this example assays were performed for gentamicin. Concentrations of tagging constituents from both ligands were measured after incubation and the ratios of the two measurements were determined to correlate with the concentration of gentamicin assay ligand. Tests were performed with two types of StiQ samplers with different optical properties. One had white transparent glue between the cellulose acetate-nitrate polymeric surface and a blue plastic substrate while the other had a black opaque glue. The StiQ samplers with white glue gave higher emission measurements. The use of the two types of StiQ samplers shows how the determination of the ratio of tag measurements can compensate for variable gain in the interface between the StiQ sampler and the fluorometer.

These tests were performed as follows: a group of StiQ samplers were spotted with TRITC-anti-gentamicin, dried and washed and dried again. A set of assay ligand samplers were prepared with the following known concentrations of gentamicin: 10, 20, 40, 80, 160 and 320 nanograms of gentamicin per 500 microliters of buffer containing 0.01 N $NaH_2PO_4$ and 0.85% NaCl at pH 7.4 To these samplers were added 100 $\mu l$ of FITC gentamicin solution containing 66 nanograms gentamicin moiety as determined by radioimmunoassay. A group of 10 samplers were incubated in each concentration of assay ligand for 30 minutes. Thereafter surface fluorescence of the samplers were measured using FIAX fluorometers to obtain values for the fluorescence (FSU) arising from rhodamine and fluorescein. Rhodamine was measured with an excitation wavelength filter of 540 nanometers and an emission wavelength filter of 570 nanometers. Fluorescein was measured with an excitation wavelength of 475 nanometers and an emission wavelength filter of 540 nanometers. No fluorescence quenching was detected. For each different concentration of assay ligand, the following determinations were made of Standard Deviation, Mean and Coefficient of Variation (CV): separately for fluorescein, rhodamine and the ratio of fluorescein to rhodamine on the StiQ samplers with both clear and black glue. A plot of the data demonstrates good correlation and compensation for differences in the optical interfaces between StiQ samplers and the fluorometer even though it was necessary to increase the gain when reading the StiQ's employing black glue by a factor of approximately 3.25 for both the fluorescein and rhodamine signals.

| | | Clear Glue Samplers | | | |
|---|---|---|---|---|---|
| Sampler # | Genta-micin[a] Concen-tration | Fluo-rescein[b], Rhodamine[c], Ratio | Stan-dard Devia-tion | Mean | CV % |
| 1–10 | 1 μg/ml | F | 7.30 | 177 | 4.1 |
| | | R | 4.29 | 179.86 | 2.4 |
| | | F/R | 0.04 | 0.98 | 4.1 |
| 11–20 | 2 μg/ml | F | 5.8 | 168 | 3.5 |
| | | R | 5.25 | 182 | 2.9 |
| | | F/R | 0.033 | 0.92 | 3.6 |
| 21–30 | 4 μg/ml | F | 5.2 | 149 | 3.5 |
| | | R | 2.875 | 183 | 1.6 |
| | | F/R | 0.02 | 0.81 | 2.4 |
| 31–40 | 8 μg/ml | F | 5.35 | 134.4 | 3.9 |
| | | R | 4.6 | 189 | 2.4 |
| | | F/R | 0.026 | 0.707 | 3.6 |
| 41–50 | 16 μg/ml | F | 2.32 | 121.06 | 1.9 |
| | | R | 2.15 | 193.7 | 1.1 |
| | | F/R | 0.009 | 0.62 | 1.4 |
| 51–60 | 32 μg/ml | F | 2.72 | 98.6 | 2.8 |
| | | R | 3.14 | 192.4 | 1.6 |
| | | F/R | 0.009 | 9.509 | 1.85 |

[a] in sample
[b] gain = 1.2
[c] gain = 2.2

| | | Black Glue Samplers | | | |
|---|---|---|---|---|---|
| Sampler # | Genta-micin[a] Concen-tration | Fluo-rescein[b], Rhodamine[c], Ratio | Stan-dard Devia-tion | Mean | CV % |
| 1–10 | 1 μg/ml | F | 3.29 | 183.4 | 1.8 |
| | | R | 5.37 | 177.9 | 3.0 |
| | | F/R | 0.02 | 1.03 | 2.2 |
| 11–20 | 2 μg/ml | F | 5.96 | 164.7 | 3.6 |
| | | R | 6.59 | 170.6 | 3.8 |
| | | F/R | 0.032 | 0.96 | 3.3 |
| 21–30 | 4 μg/ml | F | 11.18 | 146.4 | 7.6 |
| | | R | 7.05 | 166.41 | 4.2 |
| | | F/R | 0.037 | 0.88 | 4.2 |
| 31–40 | 8 μg/ml | F | 7.62 | 127.31 | 5.9 |
| | | R | 7.57 | 169.4 | 4.4 |
| | | F/R | 0.02 | 0.75 | 2.8 |
| 41–50 | 16 μg/ml | F | 3.78 | 121.81 | 3.1 |
| | | R | 5.38 | 177.08 | 3.0 |
| | | F/R | 0.03 | 0.687 | 4.2 |
| 51–60 | 32 μg/ml | F | 6.94 | 100.78 | 6.8 |
| | | R | 14.28 | 169.3 | 8.4 |
| | | F/R | 0.02 | 0.596 | 3.2 |

[a] in sample
[b] gain = 4
[c] gain = 7.1

We claim:

1. In a method of performing an immunoassay in which a receptor ligand is contacted with a test ligand which binds immunologically with the receptor ligand and the receptor and/or test ligands are contacted with an assay ligand which is capable of immunologically binding to the receptor and/or test ligand the improvement which comprises employing a receptor ligand containing a tagging constituent which is independent of the tagging constituent on the test ligand.

2. The method of claim 1 which further includes the steps of quantitatively detecting at least one of the tagged constituents after contacting the receptor ligand and the test ligand.

3. In a method of performing an immunoassay in which a receptor ligand is contacted with a test ligand which binds immunologically with the receptor ligand and the receptor and/or test ligands are contacted with an assay ligand which is capable of immunologically binding to the receptor and/or test ligand the improvement which comprises employing a receptor ligand containing a tagging constituent which is independent of the tagging constituent on the test ligand, and measuring the quantity of assay ligand by measuring the quantities of tagging constituents on both the receptor ligand and test ligand while said receptor and test ligand are immunologically bound together.

4. The method of claim 3 in which said measurement is performed by detecting fluorescent light from both the receptor and test ligands with the same fluorometer.

5. The method of claim 3 in which the receptor and/or test ligand is supported on a surface.

6. The method of claim 3 in which the two tagging constituents are formed of fluorescent materials which fluoresce at different wavelengths.

* * * * *